United States Patent [19]

Hayama et al.

[11] Patent Number: 5,098,699
[45] Date of Patent: Mar. 24, 1992

[54] HAIR SETTING GEL COMPOSITION

[75] Inventors: Kazuhide Hayama; Kanji Narazaki; Sigeoki Kawaguchi, all of Mie, Japan

[73] Assignee: Mitsubishi Petrochemical Co., Ltd., Tokyo, Japan

[21] Appl. No.: 625,684

[22] Filed: Dec. 12, 1990

Related U.S. Application Data

[63] Continuation of Ser. No. 310,649, Feb. 15, 1989, abandoned.

[30] Foreign Application Priority Data

Feb. 23, 1988 [JP] Japan .................................. 63-38665

[51] Int. Cl.$^5$ ................................................ A61K 7/11
[52] U.S. Cl. ................................ 424/71; 424/DIG. 2
[58] Field of Search ............... 424/71, 78, 81, DIG. 2; 514/944

[56] References Cited

U.S. PATENT DOCUMENTS 4,402,977 9/1983 Grollier et al. ....................... 424/71

FOREIGN PATENT DOCUMENTS 2025228 7/1979 United Kingdom .
2043077 2/1980 United Kingdom .
2098226 5/1982 United Kingdom .
2098624 5/1982 United Kingdom .

Primary Examiner—Thurman K. Page
Assistant Examiner—Amy Hulina
Attorney, Agent, or Firm—Oblon, Spivak, McClelland, Maier & Neustadt

[57] ABSTRACT

A hair setting gel composition comprising (A) from 0.2 to 5% by weight of a partially of completely neutralized salt of a crosslinked carboxyvinyl polymer, (B) from 0.5 to 10% by weight of an amphoteric resin, and (C) from 85 to 99.5% by weight of a solvent mainly comprising water and/or a lower alcohol, with the total of the components (A), (B) and (C) being 100% by weight. The gel composition is excellent in transparency and hair setting performance.

2 Claims, No Drawings

HAIR SETTING GEL COMPOSITION

This application is a continuation of application Ser. No. 310,649, filed on Feb. 15, 1989, now abandoned.

FIELD OF THE INVENTION

This invention relates to a hair setting gel composition which is excellent in transparency and hair setting performance.

BACKGROUND OF THE INVENTION

It is known that hair can be set and dressed to have a desired style by application of an atomized resin composition, a foamed resin composition (so-called mousse), a gel composition, etc.

The hair setting gel composition comprises a gel-forming base and a resin for hair setting. Gel-forming bases generally employed include crosslinked carboxyvinyl polymers. Cellulose derivatives are rarely used as gel-forming bases. As the resin for hair setting, nonionic resins are generally employed.

Hair setting resins further include cationic resins and anionic resins. However, in cases where a crosslinked carboxyvinyl polymer is used as a gel-forming base, cationic resins form an ionic complex with the anionic crosslinked carboxyvinyl polymer to thereby precipitate a polymer, failing to form a gel. Anionic resins cause destruction of a gel, i.e., viscosity reduction, which is believed to be ascribable to the counter ion site of the anion site, similarly failing to form a gel.

From these reasons, nonionic resins, e.g., a vinylpyrrolidone polymer, a vinylpyrrolidone/vinyl acetate copolymer, etc., have been employed as a hair setting resin in the conventional hair setting gels containing a crosslinked carboxyvinyl polymer as a gel-forming base. However, the hair setting gels using these nonionic resins are disadvantageous in that they easily undergo influences of humidity and are not fully satisfactory in hair setting performance. That is, while the nonionic resin in the form of a film before moisture adsorption is so hard and causes flaking (i.e., release from hair) for luck of affinity to hair, it becomes very soft at high temperatures and high humidities, resulting in not only reduction of hair setting properties but also blocking of hairs which makes combing or brushing difficult.

SUMMARY OF THE INVENTION

One object of this invention is to provide a hair setting gel composition having transparency and excellent hair setting performance.

The present invention relates to a hair setting gel composition comprising (A) from 0.2 to 5% by weight of a partially or completely neutralized salt of a crosslinked carboxyvinyl polymer, (B) from 0.5 to 10% by weight of an amphoteric resin, and (C) from 85 to 99.3% by weight of a solvent mainly comprising water and/or a lower alcohol, with the total of the components (A), (B) and (C) being 100% by weight.

DETAILED DESCRIPTION OF THE INVENTION

The crosslinked carboxyvinyl polymer which can be used in the present invention is well known as a base for forming hair setting gels as stated above and can be obtained by crosslinking polymerization of a monomer mainly comprising an unsaturated carboxylic acid (e.g., acrylic acid, methacrylic acid, itaconic acid, maleic acid) and a polyfunctional compound (e.g., ethylene glycol diacrylate, divinylbenzene, polyallyl compounds, polyepoxides). For details of the preparation of the crosslinked carboxyvinyl polymer, reference can be made to it in JP-B-32-4141 and 45-27830 (the term "JP-B" as used herein means an "examined Japanese patent publication") and JP-A-61-72706 (the term "JP-A" as used herein means an "unexamined published Japanese patent application").

The above-described crosslinked carboxyvinyl polymers are commercially available under trade names of Carbopol 934, 940, and 941 (products of B.F. Goodrich Chemical Co.), Hiviswako 103, 104 and 105 (products of Wako Pure Chemical Inds., Ltd.), Junron PW-110, 111 and 115 (products of Nippon Pure Chemical K.K.), Lubrajel (product of Gardian Chemical Co.), U-Jelly (product of Showa Denko K.K.), and so on. The object of the present invention may be achieved by utilizing these commercially available products.

The crosslinked carboxyvinyl polymers may be used either individually or in combinations of two or more thereof.

In the gel composition of the invention, the crosslinked carboxyvinyl polymer is used in the form of a partially or completely neutralized salt with an appropriate alkali (hereinafter referred to as crosslinked carboxyvinyl polymer salt).

The proportion of the crosslinked carboxyvinyl polymer salt as the component (A) in the gel composition ranges from 0.2 to 5%, preferably from 0.3 to 3%, by weight based on the total of the component (A), an amphoteric resin as the component (B), and a solvent mainly comprising water and/or a lower alcohol as the component (C). If it is less than 0.2%, the composition fails to form a gel. It is exceeds 5%, the viscosity of the composition becomes so high that workability in dissolving, dispersing, charging, or the like operation during the preparation of the hair setting gel is deteriorated and that the resulting gel is hard to handle on use.

The amphoteric resin which can be used in the present invention as the component (B) is a resin containing both an anionic moiety and a cationic moiety per polymer molecule. The amphoteric resins are divided into two types: (1) copolymers having a betaine structural unit and (2) copolymers obtained by copolymerizing at least an acidic vinyl monomer and a basic vinyl monomer and, if desired, other copolymerizable monomers.

Resins of the first type are preferred because of excellent compatibility with the crosslinked carboxyvinyl polymer salt, involving no fear of reducing gel strength.

Of the copolymer resins of the first type, preferred are those containing a betaine structure unit of formula (V) shown below and having a molecular weight of from 5,000 to 500,000, more preferably from 10,000 to 300,000, from the standpoint of satisfactory transparency and excellent hair setting performance.

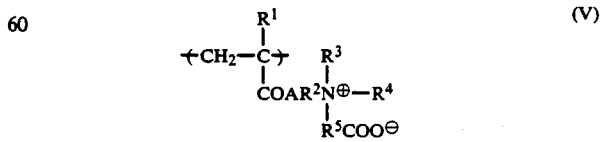

wherein A represents an oxygen atom or —NH— group; $R^1$ represents a hydrogen atom or a methyl group; $R^2$ represents an alkylene group having from 1 to 4 carbon atoms; $R^3$ and $R^4$ each represents a hydrogen atom or an alkyl group having from 1 to 4 carbon atoms; and $R^5$ represents an alkylene group having from 1 to 4 carbon atoms.

The copolymer resin having the structural unit of formula (V) can be generally prepared by copolymerizing a monomer mixture essentially comprising (i) at least one of acrylic or methacrylic acid derivatives represented by formula (I):

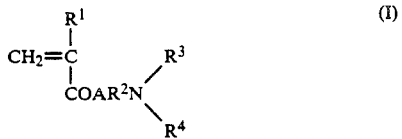

wherein A, $R^1$, $R^2$, $R^3$ and $R^4$ are as defined above, and (ii) at least one of acrylic or methacrylic esters represented by formula (II):

wherein
$R^1$ is as defined above;
and $Rd^6$ represents an alkyl, alkenyl or cycloalkyl group having from 1 to 24 carbon atoms,
and then reacting the copolymer with a halogenated fatty acid salt (amphoteric agent) represented by formula (IV):

wherein $R^5$ is as defined above: X represents a halogen atom (e.g., Cl, Br, I); and M represents an alkali metal (e.g., Na, K).

For the purpose of improving transparency of the gel composition and imparting gloss or softness to a dry film of the gel applied to hair, the monomer mixture may further comprise (iii) one or more monomers other than the monomers (i) and (ii).

Specific examples of the acrylic or methacrylic acid derivatives represented by formula (I) are dimethylaminoethyl (meth)acrylate [the term "(meth)acrylate" means acrylate and methacrylate inclusively, hereinafter the same], diethylaminoethyl (meth)acrylate, dimethylaminopropyl (meth)acrylate, dimethylaminoethyl (meth)acrylamide, and dimethylaminopropyl (meth)acrylamide.

Specific examples of the acrylic or methacrylic acid esters represented by formula (II) are methyl (meth)acrylate, ethyl (meth)acrylate, isobutyl (meth)acrylate, allyl (meth)acrylate, 2-ethylhexyl (meth)acrylate, lauryl (meth)acrylate, oleyl (meth)acrylate, stearyl (meth)acrylate, and cyclohexyl (meth)acrylate.

Included in the other monomers (iii) which are copolymerizable with the monomers (i) and (ii), if necessary, are acrylamide, N vinylpyrrolidone, hydroxyethyl or hydroxypropyl (meth)acrylate, polyethylene glycol or polypropylene glycol mono(meth)acrylate, styrene, vinyl acetate, vinyltrichlorosilane, and methacryloxypropyltrimethoxysilane.

The monomer (i) is used in an amount of from 30 to 97%, preferably from 50 to 90%, by weight based on the monomer mixture. The monomer (ii) is used in an amount of from 3 to 70% preferably from 10 to 50%, by weight based on the monomer mixture. The monomer (iii) is used in an amount of from 0 to 30%, preferably from 0 to 20%, by weight based on the monomer mixture.

Hair setting gels having satisfactory transparency and hair setting properties of the present invention can easily be obtained by using the amphoteric resin having the betaine structural unit of formula (V) and a molecular weight of from 5,000 to 500,000, which is obtained by rendering the copolymer having the above-recited copolymerization ratio amphoteric with the halogenated fatty acid salt of formula (IV).

In carrying out the preparation of the amphoteric resin having the betaine structural unit of formula (V), the above-described monomers are copolymerized in a hydrophilic solvent, and the resulting copolymer in a solution is then reacted with the halogenated fatty acid salt represented by formula (IV) to become amphoteric.

Specific examples of the halogenated fatty acid salts of formula (IV) are potassium monochloroacetate, sodium monochloroacetate, and potassium monobromopropionte.

The reaction between the copolymer and the compound of formula (IV) is carried out to a degree of conversion of at least 95%, preferably 98% or more, to thereby decrease the unreacted tertiary amine content as low as possible for assuring satisfactory transparency and hair setting properties. If the unreacted tertiary amine remains in the resin in a high proportion, it is assumed that the resin shows cationic properties in a neutral pH region and forms an ion complex with the anionic crosslinked carboxyvinyl polymer, which causes white turbidity and reduction in viscosity.

Since the product as obtained contains by-produced salts (e.g., sodium chloride, potassium chloride), the reaction mixture is subjected to centrifugal separation or filtration to remove the precipitated salts. If desired as is preferred, dissolved salts in the amphoteric resin can be removed by ion exchange treatment. Existence of dissolved salts in the amphoteric resin reduces strength of a gel formed by the crosslinked carboxyvinyl polymer during the preparation of the hair setting gel composition. It is preferable, therefore, that the dissolved salt content in the amphoteric resin be adjusted to 500 ppm or less, more preferably 50 ppm or less.

JP-B-62-32165 can be referred to with respect to the copolymerization reaction, the subsequent reaction to render the copolymer amphoteric, and the removal of dissolved salts.

The copolymer resins of the second type can be obtained by copolymerization of (vi) at least one acidic vinyl monomer and (vii) at least one basic vinyl monomer and, if desired, (viii) other copolymerizable monomer or monomers according to commonly known techniques, such as bulk polymerization, solution polymerization, suspension polymerization, and pearl polymerization.

The copolymer resin of the second type preferably has a molecular weight of from 5,000 to 500,000, more preferably from 10,000 to 300,000.

Specific examples of the acidic vinyl monomer (vi) include acrylic acid, methacrylic acid, maleic acid, itaconic acid, fumaric acid, vinylacetic acid, crotonic acid, maleic anhydride, and half esters between unsaturated polybasic acids (e.g., phthalic anhydride, oxalic anhydride) and hydroxypropyl methacrylate, hydroxyethyl acrylate, etc. These acidic vinyl monomers may be used either as they are or as partially or completely neutralized with, for example, alkali metal hydroxides (e.g., sodium hydroxide, potassium hydroxide) or amines (e.g., triethanolamine, aminomethylpropanol) to form a salt.

Specific examples of the monomer (vii) are the same as those enumerated above for the monomer (i). Specific examples of the monomer (viii) which are copolymerizable with the monomers (vi) and (vii) are the same as those enumerated above for the monomers (ii) and (iii).

The monomers (vi) and (vii) are used in a total amount of from 30 to 97%, preferably from 40 to 90%, by weight based on the monomer mixture, the molar ratio of the monomer (vi) to monomer (vii) preferably ranging from 0.7/1.3 to 1.3/0.7, more preferably from 0.8/1.2 to 1.2/0.8.

The proportion of the above-described amphoteric resin as the component (B) in the gel composition ranges from 0.5 to 10%, preferably from 1 to 8%, by weight based on the total of the components (A), (B) and (C). If it is less than 0.5%, sufficient hair setting effects cannot be produced. If it exceeds 10%, the hair treated with the gel feels stiff due to the excessive resin content.

The solvent as the component (C) mainly comprises water and/or a lower alcohol (e.g., methanol, ethanol, isopropanol) and may further contain relatively small amounts of other hydrophilic solvents (e.g., ethylene glycol, ethyl cellosolve, dioxane, methyl acetate). Particularly preferred solvents are water and mixed solvents of water and ethanol or isopropanol.

The proportion of the solvent as the component (C) in the gel composition ranges from 85 to 99.3%, preferably from 89 to 98.7%, based on the total of the components (A), (B) and (C).

In the present invention, a base is used for pH adjustment, and particularly for partial or complete neutralization of the crosslinked carboxyvinyl polymer. Bases to be used include alkanolamines, e.g., 2-amino-2-methyl-1-propanol, 2-amino-2-methyl-1,3-propanediol, triethanolamine, diisopropanolamine; alkali metal hydroxides, e.g., sodium hydroxide, potassium hydroxide; basic amino acids, e.g., arginine, lysine; and ammonia. Generally employed of them ar 2-amino-2-methyl-1-propanol, diisopropanolamine, and sodium hydroxide.

The hair setting gel composition according to the present invention can be prepared usually by dissolving the crosslinked carboxyvinyl polymer in a solvent mainly comprising water and/or a lower alcohol, adding a base to the solution to at least partially neutralize the polymer to form a gel, and then adding the amphoteric resin to the gel. Alternatively, the crosslinked carboxyvinyl polymer and the amphoteric resin are dissolved in the solvent, and the base is then added thereto in an amount enough to neutralize the crosslinked carboxylvinyl polymer at least partially, i.e., enough to adjust the gel composition to a pH between 4 and 10.

If desired, the hair setting gel composition of the present invention may further contain various additives in addition to the essential components (A), (B) and (C). Implicit in such additives are those used for softening, lubricating, gloss control, and the like, e.g., lanolin, lanolin derivatives, glycerin, glycerin derivatives, isopropyl myristate, oleyl alcohol, dibutyl phthalate, silicone derivatives, polyethylene glycol, polyethylene glycol derivatives, and pantothenyl alcohol; surface active agents, flavors, colorants, antiseptics, chips of colored film, pigments, and others commonly employed in the art.

If desired, the hair setting gel composition may furthermore contain various other polymers, such as cationic, anionic, and nonionic polymers, as long as they should no impair hair setting performances of the composition.

The present invention is now illustrated in greater detail with reference to the following Preparation Example, Examples, and Comparative Examples, but it should be understood that the present invention is not deemed to be limited thereto. In these examples, all the parts and percents are by weight unless otherwise indicated.

PREPARATION EXAMPLE 1

In a five-necked flask equipped with a reflux condenser, a dropping funnel, a thermometer, a glass tube for displacement with nitrogen, and a stirrer were charged 75 parts of dimethylaminoethyl methacrylate, 10 parts of methyl methacrylate, 10 parts of isobutyl methacrylate, 5 parts of stearyl methacrylate, and 100 parts of ethanol, and 0.6 part of $\alpha,\alpha'$-azobisisobutyronitrile was added thereto. The mixture was heat-refluxed at 80° C. in a nitrogen stream for 4 hours to effect polymerization.

A 50% ethanol suspension containing potassium monochloroacetate in an amount 5% excess of the mole of the dimethylaminoethyl methacrylate was added dropwise to the reaction mixture through the dropping funnel. The mixture was again heated at 80° C. for 8 hours in a nitrogen stream to render the polymer amphoteric.

The resulting viscous suspension was filtered under pressure by the use of a filter of Nippon Senshoku Kikai K.K. to remove the precipitate. The filtrate was passed through a column packed with a regenerated cation exchange resin ("Diaion PK-220" produced by Mitsubishi Chemical Inds., Ltd.; the system was replaced with ethanol after regeneration) and then through a column packed with a regenerated anion exchange resin ("Diaion PA 416" produced by Mitsubishi Chemical Inds., Ltd.; the system was replaced with ethanol after regeneration). To the pale yellow transparent effluent was added ethanol to adjust the resinous content to 30% to obtain an amphoteric resin solution. The resulting solution was designated as Resin Solution $B_1$.

The resin in Resin Solution $B_1$ was found to have a molecular weight of 70,000 by gel permeation chromatography (GPC), and the degree of conversion was 99.5%.

PREPARATION EXAMPLE 2

Resin Solution $B_2$ was obtained in the same manner as in Preparation Example 1, except for changing the amount of potassium monochloroacetate to 75% of the mol of the dimethylaminoethyl methacrylate.

The degree of conversion of the amphoteric resin was 71%.

PREPARATION EXAMPLE 3

In the same flask as used in Preparation example 1 were charged 50 parts of diethylaminoethyl methacrylate, 10 parts of methyl acrylate, 20 parts of methyl methacrylate, 10 parts of butyl methacrylate, 10 parts of lauryl methacrylate, and 65 parts of isopropanol. To the mixture was added 0.6 part of 2,2'-azobis(2,4-dimethylvaleronitrile), and the mixture was heated at 70° C. for 2 hours and then at reflux (80° C.) for 2 hours to effect polymerization.

A 50% isopropanol suspension containing sodium monochloroacetate in an amount 5% excess of the mole of the diethylaminoethyl methacrylate was added dropwise to the reaction mixture through the dropping funnel, and the mixture was further heated at 80° C. in a nitrogen stream for 8 hours to convert the polymer amphoteric. The resulting viscous suspension was filtered to remove the precipitate in the same manner as in Preparation Example 1.

The filtrate was transferred to a flask equipped with a distillation tube, and the isopropanol was distilled off while adding pure water to thereby displace the isopropanol with water to obtain a pale yellow transparent amphoteric resin aqueous solution having a resinous content of 20%. The resulting solution was designated as Resin Solution B₃.

The resin in Resin Solution B₃ was found to have a molecular weight of 150,000 as measured by GPC, and the degree of conversion was 99%.

PREPARATION EXAMPLE 4

Resin Solution B₄ was prepared in the same manner as in Preparation Example 1, except for starting with a monomer mixture consisting of 60 parts of dimethylaminoethyl methacrylate, 20 parts of methyl methacrylate, and 20 parts of methoxypolyethylene glycol (n=9) methacrylate.

The resulting amphoteric resin was found to have a molecular weight of 100,000 as measured by GPC, and the degree of conversion was 99.9%.

PREPARATION EXAMPLE 5

In the same flask as used in Preparation Example 1 were charged 30 parts of diethylaminoethyl methacrylate, 15 parts of acrylic acid, 10 parts of ethyl methacrylate, 10 parts of allyl acrylate 35 parts of isobutyl methacrylate, and 200 parts of ethanol, and 1 part of α,α'-azobisisobutyronitrile was added thereto. The mixture was heat-refluxed at 80° C. for 5 hours in a nitrogen stream to effect polymerization.

The resulting pale yellow transparent solution was diluted with ethanol to adjust the resinous content to 30%. This solution was designated as Resin Solution B₅.

The amphoteric resin was found to have a molecular weight of 150,000 as measured by GPC.

EXAMPLE 1

In 90.7 g of pure water was dissolved 0.5 g of a commercially available crosslinked carboxyvinyl polymer ("Carbopol 940", a trade name of B.F. Goodrich Chemical Co.), and 1.8 g of a 10% aqueous solution of sodium hydroxide was added thereto as a base, followed by stirring. To the solution was added 7 g of Resin Solution B₁ as prepared in Preparation Example 1, followed by uniformly stirring to obtain a hair setting gel.

The resulting hair setting gel was evaluated according to the following test methods, and the results obtained are shown in Table 1. Table 1 demonstrates excellent performances of the hair setting gel.

a) Transparency

The hair setting gel was put in a glass bottle, and its transparency was evaluated with eyes and rated according to the following scale.

Good; Satisfactorily transparent

Medium; Slight haze was observed

Poor; White trubidity was observed b) Viscosity

A Brookfield viscometer (revolutions per minute=20) was used for measurement. The viscosity of the hair setting gel was measured at 25° C. when five revolutions were given to the viscometer.

c) Curl Retention

The hair setting gel was applied uniformly to a 23 cm long straight hair (2 g) taken from the head of a Japanese, and the excess was removed by strongly squeezing between fingers. Immediately thereafter, the hair was wound around a rod having a diameter of 1.2 cm and dried at 50° C. for 1 hour. After removal from the rod, the hair was vertically suspended in a thermo-hygrostat at 30° C. and 90% RH and allowed to stand for 3 hours. The length of the curled hair as suspended was determined before and after the 3-hour standing, and a curl retention (%) was calculated therefrom according to equation:

$$\text{Curl Retention (\%)} = \frac{L - L_3}{L - L_0} \times 100$$

wherein L is a length of the straight hair (23 cm); $L_0$ is a length (cm) of the curled hair immediately after removal from the rod; and $L_3$ is a length (cm) of the curled hair after standing in the thermo-hygrostat for 3 hours.

d) Flaking

The hair setting gel was uniformly applied to straight hair (each hair had a length of 23 cm and a weight of 2 g) taken from the head of a Japanese and squeezed between fingers to remove the excess. The hair was dried at 50° C. for 1 hour and allowed to stand in an atmosphere of 23° C. and 60% RH for a whole day.

The hair was combed 10 times in an atmosphere of 23° C. and 60% RH, and both the hair and the comb were observed with eyes to evaluate the flaking of the film, i.e., release of the film from the hair. Evaluations were made according to the following rating system.

Good; No or substantially no flaking was observed.

Medium; Flaking was observed.

Bad; Considerable flaking was observed.

EXAMPLE 2 TO 7

A hair setting gel was prepared in the same manner as in Example 1, except for using a composition shown in Table 1. Each of the resulting gel compositions was evaluated in the same manner as in Example 1, and the results obtained are shown in Table 1.

COMPARATIVE EXAMPLES 1 TO 4

A hair setting gel was prepared in the same manner as in Example 1, except that the amphoteric resin was not used or replaced with polyvinylpyrrolidone (nonionic resin), an acrylic polymer (anionic resin) or a diallyldimethylammonium chloride polymer (cationic resin) as shown in Table 1.

Each of the resulting gel compositions was evaluated in the same manner as in Example 1, and the results obtained are shown in Table 1.

As can be seen from Table 1, the gel containing only the crosslinked carboxyvinyl polymer neutralized product but no resin (Comparative Example 1) has poor setting properties (i.e., curl retention); the gel containing the nonionic resin (Comparative Example 2) not only exhibits insufficient setting properties but undergoes considerable flaking; the gel containing the anionic resin (Comparative Example 3) is poor in transparency, has too a low viscosity to retain a geled state, and undergoes flaking; and the gel containing the cationic resin (Comparative Example 4) suffers from precipitation of the polymer, failing to retain a geled state and to exhibit sufficient setting properties.

out causing flaking. Further, the film is free from temperature influences and, therefore, causes no blocking even under high temperature and high humidity conditions.

While the invention has been described in detail and with reference to specific embodiments thereof, it will be apparent to one skilled in the art that various changes and modifications can be made therein without depart-

TABLE 1

| | Hair Setting Gel Composition | | | | Results of Evaluation | | | |
|---|---|---|---|---|---|---|---|---|
| | Component (A) (g) | Component (B) (g) | Base (g) | Solvent (g) | Transparency | Viscosity (cps) | Curl Retention (%) | Flaking |
| Example No. | | | | | | | | |
| 1 | Carbopol 940 (0.5)*1 | Resin Solution $B_1$ (7) | NaOH (10% aq. solution) (1.8) | Pure water (90.7) | good | 59,000 | 82 | good |
| 2 | Carbopol 940 (0.5) | Resin Solution $B_2$ (7) | NaOH (10% aq. solution) (1.8) | Pure water (90.7) | medium | 58,000 | 78 | good |
| 3 | Carbopol 940 (2) | Resin Solution $B_3$ (10) | NaOH (10% aq. solution) (7.2) | Pure water (80.8) | good | 45,000 | 85 | good |
| 4 | Carbopol 940 (0.5) | Resin Solution $B_4$ (10) | NaOH (10% aq. solution) (1.0) | Pure water (91.5) | good | 60,000 | 80 | good |
| 5 | Carbopol 940 (3) | Resin Solution $B_5$ (7) | NaOH (10% aq. solution) (12.6) | Pure water (77.4) | medium | 33,000 | 72 | medium |
| 6 | Hiviswako 104 (0.5)*2 | Resin Solution $B_1$ (10) | 2-amino-2-methyl-1-propanol (10% aq. solution) (4) | Pure water (85.5) | good | 63,000 | 85 | good |
| 7 | Hiviswako 104 (1.0) | Resin Solution $B_4$ (10) | diisopropanolamine (10% aq. solution) (10) | Pure water (59) ethanol (20) | good | 75,000 | 77 | medium |
| Compar. Example No. | | | | | | | | |
| 1 | Carbopol 940 (0.5)*1 | — | NaOH (10% aq. solution) (1.8) | Pure water (97.7) | good | 55,000 | 20 | medium |
| 2 | Carbopol 940 (0.5) | PVPK-30 (2)*3 | NaOH (10% aq. solution) (1.8) | Pure water (95.7) | good | 57,000 | 34 | bad |
| 3 | Carbopol 940 (0.5) | Diahold HR-200 (4)*4 | NaOH (10% aq. solution) (1.8) | Pure water (93.7) | medium to poor | 2,300 | 65 | bad to medium |
| 4 | Carbopol 940 (0.5) | MERQUAT 100 (5)*5 | NaOH (10% aq. solution) (1.8) | Pure water (92.7) | poor | 700 | 28 | good |

Note:
*1 A trade name of B. F. Goodrich Chemical Co.
*2 A trade name of Wako Pure Chemical Inds., Ltd.
*3 A polyvinyl pyrrolidone powder, produced by BASF A.G.
*4 A 50% ethanol solution of an acrylic polymer, produced by Mitsubishi Petrochemical Co., Ltd.
*5 A 40% aqueous solution of a diallyldimethylammonium chloride polymer, produced by Merk Co.

As described above and demonstrated in the foregoing Examples, the hair setting gel compositions according to the present invention exhibit satisfactory transparency and, when applied to hair, form a soft film having excellent setting performance even under high temperature and high humidity conditions. The film of the hair setting gel facilitates combing or brushing without causing flaking. Further, the film is free from temperature influences and, therefore, causes no blocking even under high temperature and high humidity conditions.

ing from the spirit and scope thereof.

What is claimed is:

1. A hair setting gel composition comprising (A) from 0.2 to 5% by weight of a partially or complete neutralized salt of a crosslinked carboxyvinyl polymer, (B)

from 0.5 to 10% by weight of an amphoteric resin containing a betaine structure of formula (V):

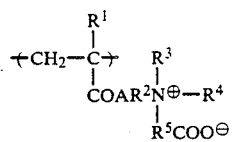  (V)

wherein A represents an oxygen atom or —NH— group; $R^1$ represents a hydrogen atom or a methyl group; $R^2$ represents an alkylene group having from 1 to 4 carbon atoms; $R^3$ and $R^4$ each represents a hydrogen atom or an alkyl group having from 1 to 4 carbon atoms; and $R^5$ represents an alkylene group having from 1 to 4 carbon atoms, said resin having a molecular weight of from 5,000 to 500,000, and (C) from 85 to 99.3% by weight of a solvent mainly comprising water and/or a lower alcohol, with the total of the components (A), (B) and (C) being 100% by weight.

2. A hair setting gel composition as claimed in claim 1, wherein said solvent is water or a mixed solvent of water and ethanol or isopropanol.

* * * * *